US012337170B2

(12) United States Patent
Sorenson et al.

(10) Patent No.: US 12,337,170 B2
(45) Date of Patent: Jun. 24, 2025

(54) IMPLANTABLE MEDICAL LEADS WITH A TWISTED PAIR OF CONDUCTORS

(71) Applicant: MEDTRONIC, INC., Minneapolis, MN (US)

(72) Inventors: Brian J. Sorenson, New Brighton, MN (US); Simon E. Goldman, Louis Park, MN (US); Gregory P. Shipe, Plymouth, MN (US); Leroy L. Perz, Maple Grove, MN (US); Stephanie L. Sanford, Ham Lake, MN (US); Jonathan D. Edmonson, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 402 days.

(21) Appl. No.: 17/848,174

(22) Filed: Jun. 23, 2022

(65) Prior Publication Data

US 2022/0409883 A1    Dec. 29, 2022

Related U.S. Application Data

(60) Provisional application No. 63/214,475, filed on Jun. 24, 2021.

(51) Int. Cl.
*A61N 1/05* (2006.01)
*A61N 1/08* (2006.01)

(52) U.S. Cl.
CPC .............. *A61N 1/05* (2013.01); *A61N 1/086* (2017.08)

(58) Field of Classification Search
None
See application file for complete search history.

(56) References Cited

U.S. PATENT DOCUMENTS

| | | | |
|---|---|---|---|
| 6,374,141 B1* | 4/2002 | Sass | A61N 1/05 607/116 |
| 7,092,764 B2 | 8/2006 | Williams et al. | |
| 7,366,556 B2* | 4/2008 | Brister | A61B 5/14865 600/347 |
| 7,734,354 B1* | 6/2010 | Cox | A61N 1/05 607/116 |
| 8,639,352 B2* | 1/2014 | Wang | A61N 1/0472 607/116 |

(Continued)

FOREIGN PATENT DOCUMENTS

EP    2719422    4/2014
WO    2007/022192    2/2007

*Primary Examiner* — Carl H Layno
*Assistant Examiner* — Manolis Pahakis
(74) *Attorney, Agent, or Firm* — Shumaker & Sieffert, P.A.

(57) ABSTRACT

Implantable medical systems that include an implantable medical lead coupled to an implantable medical device for purposes of electrical stimulation therapy and/or sensing of physiological signals includes at least one twisted pair of conductors within the implantable medical lead. The twisted pair corresponds to a stimulation or sensing channel of the implantable medical device. The twisted pair provides attenuation of electromagnetic interference noise that is present at the lead or lead extension. The twisted pair may be present in a lumen of the implantable medical lead or encapsulated by the lead body. The twisted pair, along with any other conductors of the lead, may be of a linear configuration or may be coiled.

16 Claims, 5 Drawing Sheets

(56) References Cited

U.S. PATENT DOCUMENTS

| | | |
|---|---|---|
| 8,886,336 B2 | 11/2014 | Lim et al. |
| 9,031,671 B2 | 5/2015 | Wong, Sr. |
| 9,370,653 B2 | 6/2016 | Sefkow et al. |
| 9,409,008 B2 * | 8/2016 | Li .......................... C22F 1/183 |
| 9,659,679 B2 | 5/2017 | McIntyre et al. |
| 9,717,902 B2 | 8/2017 | Olliver |
| 10,183,161 B2 | 1/2019 | Shan et al. |
| 10,384,050 B2 | 8/2019 | Kamarajugadda et al. |
| 2007/0088416 A1 * | 4/2007 | Atalar .................... A61B 18/14 |
| | | 607/115 |
| 2008/0262584 A1 * | 10/2008 | Bottomley ........... A61N 1/0488 |
| | | 29/605 |
| 2010/0204767 A1 * | 8/2010 | Zhao ....................... A61N 1/05 |
| | | 607/122 |
| 2012/0182014 A1 | 7/2012 | Rivera et al. |
| 2015/0314123 A1 * | 11/2015 | Sharma ................... A61N 1/05 |
| | | 607/116 |
| 2021/0102335 A1 * | 4/2021 | Mitchell ............. D07B 1/0673 |

\* cited by examiner

IMPLANTABLE MEDICAL LEADS WITH A TWISTED PAIR OF CONDUCTORS

RELATED APPLICATIONS

The present application claims priority to U.S. Provisional Application No. 63/214,475 filed Jun. 24, 2021, which is incorporated by reference herein.

TECHNICAL FIELD

Embodiments relate to implantable medical leads that have at least one twisted pair of conductors connected to distal electrodes.

BACKGROUND

Implantable medical systems that include an implantable medical device and an implantable medical lead provide therapy to and/or monitoring of physiological conditions. Typically, the implantable medical device is implanted at a location of convenience which may be some distance from the target area to be stimulated or sensed. The implantable medical lead is implanted by being routed to the target area so that a distal end of the implantable medical lead has electrodes at the target area to deliver stimulation signals and/or sense physiological signals.

Conductors within the implantable medical lead carry electrical signals between electrical contacts on a proximal end and the electrodes located at the distal end of the lead. The proximal end is connected to the implantable medical device. Where the lead is not long enough to extend from the target area to the implantable medical device, a lead extension may be used where the proximal end of the lead connects to the distal end of the lead extension and the proximal end of the lead extension connects to the implantable medical device.

As the implantable medical lead, as well as the lead extension when present, may extend over some distance within the body of the patient, the lead and/or lead extension may be exposed to various sources of electromagnetic interference (EMI) noise that may couple onto the conductors of the lead and/or lead extension. While some degree of EMI noise will typically be present and can be attenuated by the circuitry of the implantable medical device, a large amount of noise may occur in certain situations that may hinder the ability of the implantable medical device to effectively sense physiological signals. For instance, sensing relatively small amplitude neurological signals becomes difficult where relatively large amplitude EMI noise, such as EMI noise produced by activity of the heart, is present at the implantable medical lead and/or lead extension. Furthermore, in certain circumstances, such noise may couple to the conductors and appear at the distal electrodes to potentially interfere with the delivery of stimulation therapy.

SUMMARY

Embodiments address issues such as these and others by providing an implantable medical lead that includes at least one twisted pair of electrical conductors. The twisted pair has a first conductor of the twisted pair electrically connected to a first proximal connector and a second conductor of the twisted pair electrically connected to a second proximal connector. For instance, the twisted pair may be used for a balance stimulation channel or a balanced sensing channel. EMI noise that reaches the twisted pair is attenuated at least by virtue of field cancellation produced by the twisted pair.

Embodiments provide an implantable medical lead that includes a lead body, a first proximal connector located on a proximal end of the lead body, and a second proximal connector located on the proximal end of the lead body and spaced apart from the first proximal connector. The implantable medical lead further includes a first distal electrode located on a distal end of the lead body and a second distal electrode located on the distal end of the lead body and spaced apart from the first distal electrode. Additionally, the implantable medical lead includes a twisted pair of first and second conductors with insulation separating the first and second conductors, the twisted pair being present within the lead body, the first conductor of the twisted pair electrically connecting the first proximal connector and the first distal electrode, and the second conductor of the twisted pair electrically connecting the second proximal connector to the second distal electrode.

Embodiments provide an implantable medical system that includes an implantable medical device including electrical circuitry and an implantable medical lead coupled to the implantable medical device. The implantable medical lead includes a lead body, a first proximal connector located on a proximal end of the lead body that is present within the implantable medical device, the first proximal connector being electrically coupled to the electrical circuitry, and a second proximal connector located on the proximal end of the lead body and spaced apart from the first proximal connector, the second proximal connector being electrically coupled to the electrical circuitry. The implantable medical lead further includes a first distal electrode located on a distal end of the lead body and a second distal electrode located on the distal end of the lead body and spaced apart from the first distal electrode. The implantable medical lead also includes a twisted pair of first and second conductors with insulation separating the first and second conductors, the twisted pair being present within the lead body, the first conductor of the twisted pair electrically connecting the first proximal connector and the first distal electrode, and the second conductor of the twisted pair electrically connecting the second proximal connector to the second distal electrode.

Embodiments provide a method of sensing physiological signals that involves sensing a physiological signal as a difference between a first electrical potential on a first proximal connector of an implantable medical lead and a second electrical potential on a second proximal connector of the implantable medical lead. A first electrical conductor connects the first proximal connector to a first distal electrode of the implantable medical lead, and a second electrical conductor connects the second proximal connector to a second distal electrode. The first electrical conductor and the second electrical conductor form a twisted pair with insulation between the first electrical conductor and the second electrical conductor, and wherein the twisted pair results in common mode rejection of noise occurring on the first electrical conductor and the second electrical conductor during the sensing.

DETAILED DESCRIPTION

Embodiments provide for reduced electromagnetic interference by including at least one twisted pair of conductors within an implantable medical lead. The twisted pair of conductors may correspond to a stimulation channel or a sensing channel so that the EMI is reduced for that channel. Additional channels of stimulation and/or sensing may also utilize twisted pairs of conductors within a given lead to also reduce EMI for those channels.

Figure 1:
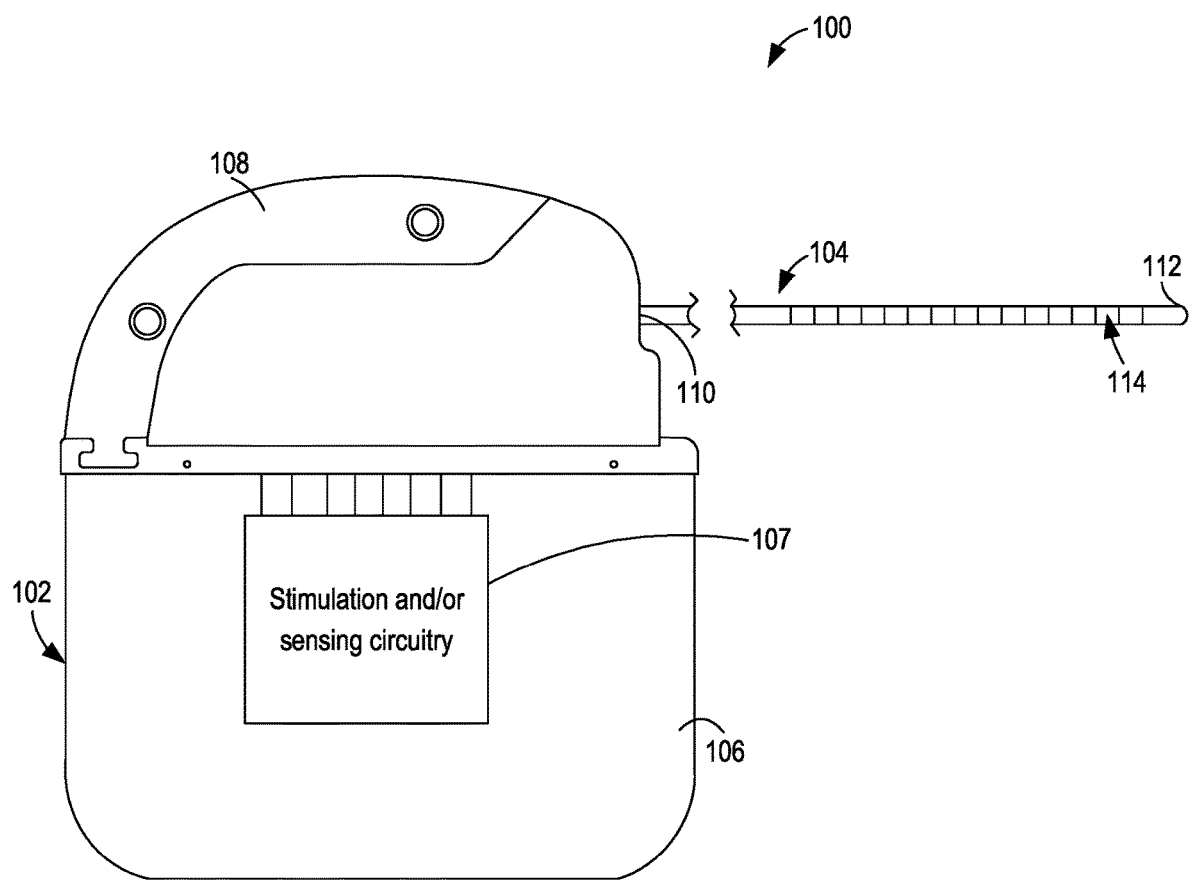
FIG. 1 shows an example of an implantable medical system that includes an implantable medical device and an embodiment of an implantable medical lead.

FIG. 1 shows an example of an implantable medical system 100 that includes an implantable medical device 102 and an implantable medical lead 104. The implantable medical system 100 may be of any type such as a neuromodulation stimulation and/or sensing system, a cardiac stimulation and/or sensing system, and the like. The implantable medical lead 104 and/or lead extension includes a proximal end that is installed into a lead passageway 110 of a header 108 of the implantable medical device 102. The header 108 is a housing for electrical contacts and is installed on a separately sealed housing 106 of the implantable medical device 102 that includes stimulation and/or sensing electrical circuitry 107.

As shown in subsequent figures and discussed below, the proximal end of the lead 104 and/or lead extension has electrical connectors. These electrical connectors engage electrical contacts within the header 108 that are electrically coupled through a feedthrough assembly from the header 108 and to the electrical circuitry 107. Conductors within the lead 104 then carry the electrical signals between the circuitry 107 of the housing 106 and electrodes 114 on a distal end 112 of the lead 104. The distal end 112 is positioned at the target stimulation and/or sensing site within the body.

Figure 2:
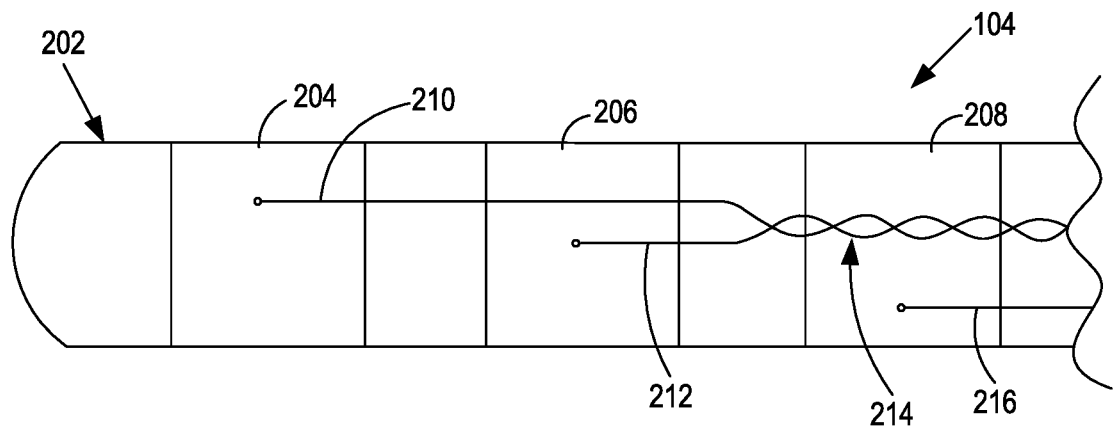
FIG. 2 shows an example of a proximal end of the implantable lead or implantable lead extension that is coupled to the implantable medical device.

FIG. 2 shows an example of a proximal end 202 of the implantable medical lead 104 and/or lead extension. The proximal end 202 includes several proximal connectors 204, 206, 208, and so on that are spaced apart from each other along the proximal end 202 to provide electrical isolation. The proximal end 202 is inserted into the lead passageway 110 of the implantable medical device 102 so that electrical connectors 204, 206, 208 and so on located on the proximal end 202 can engage electrical contacts of the implantable medical device 102. Each of the proximal connectors 204, 206, 208, and so on have an associated electrical conductor to electrically interconnect the proximal connectors to distal electrodes.

Figure 3:
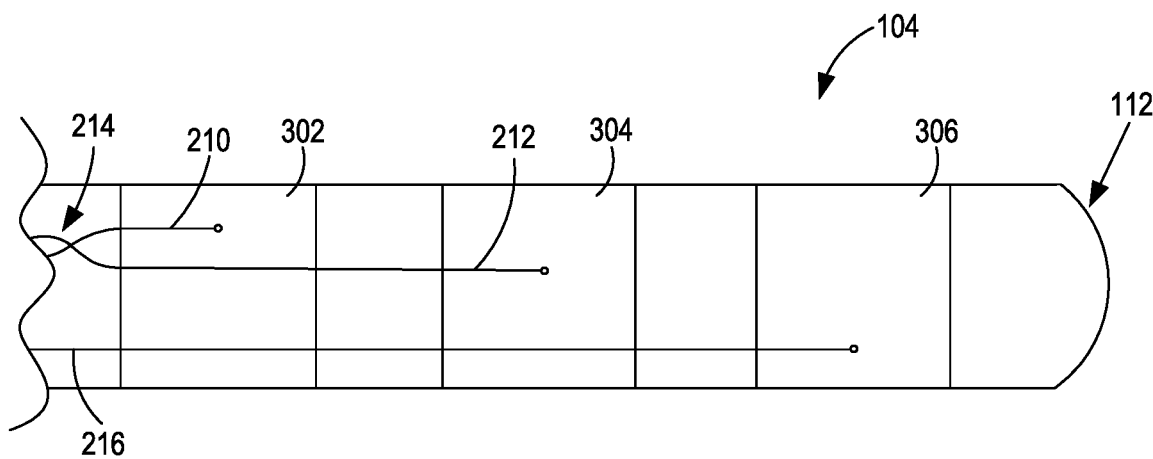
FIG. 3 shows an example of a distal end of the implantable lead that is coupled to the implantable medical device or the lead extension.

FIG. 3 shows an example of a distal end 112 of the implantable medical lead 104. The distal end includes several distal electrodes 302, 304, 306, and so on that are spaced part from each other along the distal end 112 to provide electrical isolation. The distal end 112 is positioned at the target area within the body of the patient so that electrodes 302, 304, 306 and so on located on the distal end 112 can engage body tissue to either deliver electrical stimulation therapy pulses through the tissue or to sense electrical physiological signals emanating from the tissue. Each of the distal electrodes 302, 304, 306, and so on have an associated electrical conductor attached thereto electrically interconnect the proximal connectors to distal electrodes.

Referring to both FIG. 2 and FIG. 3, in this example, a conductor 210 electrically interconnects the proximal connector 204 to the distal electrode 302. A conductor 212 electrically interconnects the proximal connector 206 to the distal electrode 304. A conductor 216 interconnects the proximal connector 208 to the distal electrode 306, and so on. The conductors may be constructed of electrically conductive material such as various metals such as platinum-iridium alloys, carbon, nickel-cobalt, and the like. These conductors 210, 212, 216, and so on are individually insulated such as by having a non-conductive coating or other insulator on the conductors 210, 212, 216 to avoid short circuits between conductors. The insulative coating or insulation may be of materials such as polytetrafluoroethylene (PTFE), ethylene tetrafluoroethylene (ETFE), silicone rubber, polyimide, and the like as well as polyurethane, poly ether block amid, and thermoplastic copolyester particularly in acute implantation scenarios. Because these conductors are individually insulated, they may co-exist within the lead 104 where contact between the conductor 210, 212, 216 may occur.

For embodiments disclosed herein, the individual insulation for the conductors allows relevant pairs of them to be put into contact intentionally in the form of twisted pairs. As can be seen in the example of FIGS. 2 and 3, the conductors 210 and 212 are twisted into a twisted pair 214. The conductors 210 and 212 correspond to a particular stimulation or sensing channel so that the twisted pair 214 of the conductors 210 and 212 provides a manner of attenuating EMI noise for the channel.

There are significant benefits of attenuating the EMI noise via the twisted pair 214. For a stimulation channel, this attenuates the amount of EMI noise that is delivered to the tissue at the target area. For a sensing channel, this attenuates the amount of EMI noise that is received into the inputs of the sensing amplifier. For instance, a sensing circuit may employ a differential input amplifier which performs a sensing of a physiological signal as a difference between a first electrical potential being provided from a first distal electrode and associated proximal connector to a first amplifier input and a second electrical potential being provided from a second distal electrode and associated proximal connector to a second amplifier input. Preventing EMI noise equally on both inputs is helpful. Furthermore, to the extent EMI noise is still present to some degree at the amplifier differential inputs, the twisted pair 214 may also allow the EMI noise to be more evenly present on the two conductors 210, 212 so that common mode rejection occurs at the differential inputs of the sensing amplifier to further filter the EMI noise from the resulting sensed signal.

Figure 4:
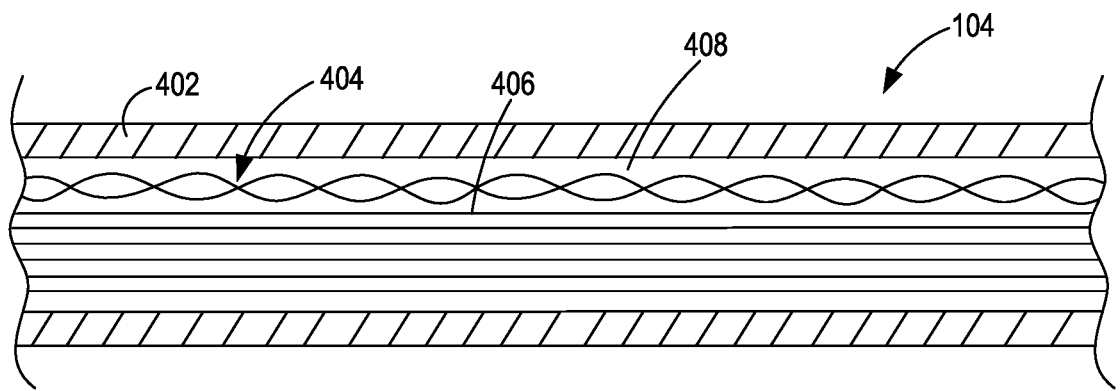
FIG. 4 is a cross-sectional view of a first example of an intermediate section of the implantable medical lead or lead extension where a twisted pair of conductors is present within a lumen of the implantable medical lead.

FIG. 4 shows an example of an intermediate section of the lead 104 or lead extension where all conductors are present. In this example, the lead 104 includes a lead body 402 made of a biocompatible material such as a polyurethane. This example of the lead 104 includes a stylet lumen 408. The conductors of this example are present within the lumen 408. In this example there is one twisted pair 404 of conductors in a linear configuration and then a set of six linear conductors 406. Therefore, there can be four simultaneous channels for a combination of bipolar stimulation and sensing utilizing eight proximal connectors and eight distal electrodes. It will be appreciated that any number of conductors, proximal connectors, and distal electrodes are possible. The twisted pair 404 and the linear conductors co-exist within the lumen 408 as each of the conductors are individually insulated as previously discussed.

The configuration of the twisted pair 404 as shown in FIG. 4 may vary. For example, the twisted pair may have a number of twists per unit length that is different than that shown. In one example where the conductor size is within the range of 0.0005 inch to 0.005 inch, the number of twists per unit length ranges from one turn for every inch of length of the lead 104 to one turn for every two inches of length of the lead 104. It will be appreciated that the number of twists per unit length may vary greatly depending upon various considerations such as conductor size, lead length, degree of attenuation desired, degree of lead flexibility, and so forth.

Figure 5:
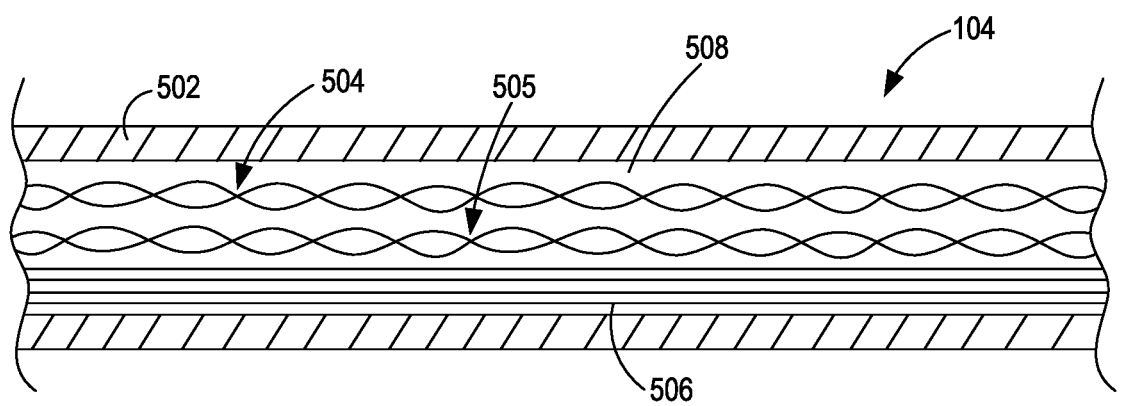
FIG. 5 is a cross-sectional view of a second example of an intermediate section of the implantable medical lead or lead extension where multiple twisted pairs of conductors are present within the implantable medical lead.

FIG. 5 shows an example of an intermediate section of the lead 104 or lead extension where all conductors are present. In this example, the lead 104 includes a lead body 502 made of a biocompatible material such as a polyurethane. This example of the lead 104 includes a stylet lumen 508. The conductors of this example are also present within the lumen 508. In this example there is a first twisted pair 504 of conductors and a second twisted pair of conductors 505 and then a set of four linear conductors 506. In this example, the two twisted pairs 504 and 505 are identical including the number of twists per unit length of the lead 104. With the eight conductors, there can again be four simultaneous channels for a combination of bipolar stimulation and sensing utilizing eight proximal connectors and eight distal electrodes. It will again be appreciated that any number of conductors, proximal connectors, and distal electrodes are possible. The twisted pairs 504 and 505 and the linear conductors co-exist within the lumen 508 as each of the conductors are individually insulated as previously discussed.

The configuration of the twisted pairs 504 and 505 as shown in FIG. 5 may also vary. For example, the twisted pairs 504 and 505 may each have a number of twists per unit length that is different than that shown. The ranges for the number of twists per unit length of lead 104 as discussed above for FIG. 4 are applicable here as well for both the twisted pair 504 and the twisted pair 505.

Figure 6:
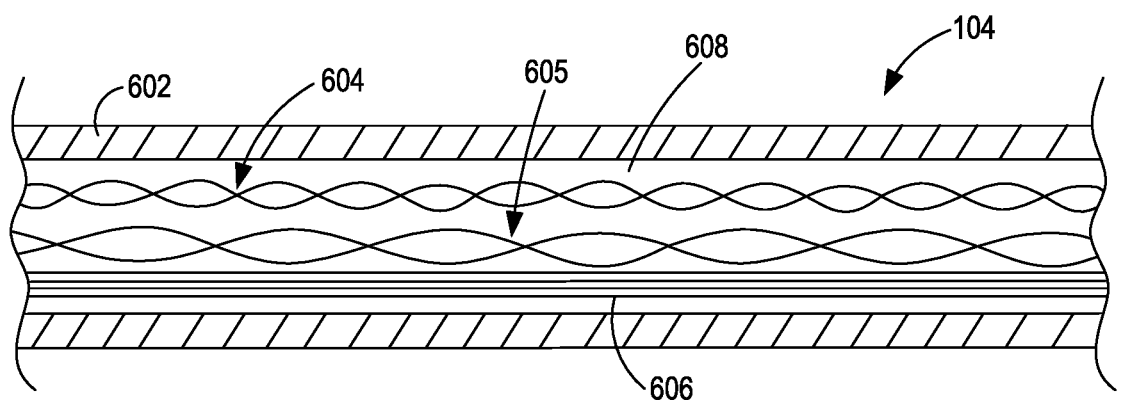
FIG. 6 is a cross-sectional view of a third example of an intermediate section of the implantable medical lead or lead extension where multiple twisted pairs of conductors with different twist rates are present within the implantable medical lead.

FIG. 6 shows another example of an intermediate section of the lead 104 or lead extension where all conductors are present. In this example, the lead 104 includes a lead body 602 made of a biocompatible material such as a polyurethane. This example of the lead 104 includes a stylet lumen 608. The conductors of this example are also present within the lumen 608. In this example there is a first twisted pair 604 of conductors and a second twisted pair of conductors 605 and then a set of four linear conductors 606. However, in this example, the twisted pairs 604 and 605 are not identical. Instead, the twisted pair 605 half the number of twists per unit length of lead 104 as the twisted pair 604. Such a difference in the number of turns per unit length may attenuate the amount of twisted pair-to-twisted pair coupling that occurs to further attenuate noise. With the eight conductors, there can again be four simultaneous channels for a combination of bipolar stimulation and sensing utilizing eight proximal connectors and eight distal electrodes. It will again be appreciated that any number of conductors, proximal connectors, and distal electrodes are possible. The twisted pairs 604 and 605 and the linear conductors again may co-exist within the lumen 608 as each of the conductors are individually insulated as previously discussed.

The configuration of the twisted pairs 604 and 605 as shown in FIG. 6 may also vary. For example, the twisted pairs 604 and 605 may each have a number of twists per unit length that are different than that shown, although on twisted pair will continue to have a different number of twists per unit length than the other twisted pair. The ranges for the number of twists per unit length of lead 104 as discussed above for FIG. 4 are applicable here as well. For instance, the twisted pair 604 may have one twist per inch of length of the lead 104 while the twisted pair 605 may have one twist per two inches of length of the lead 104.

Figure 7:
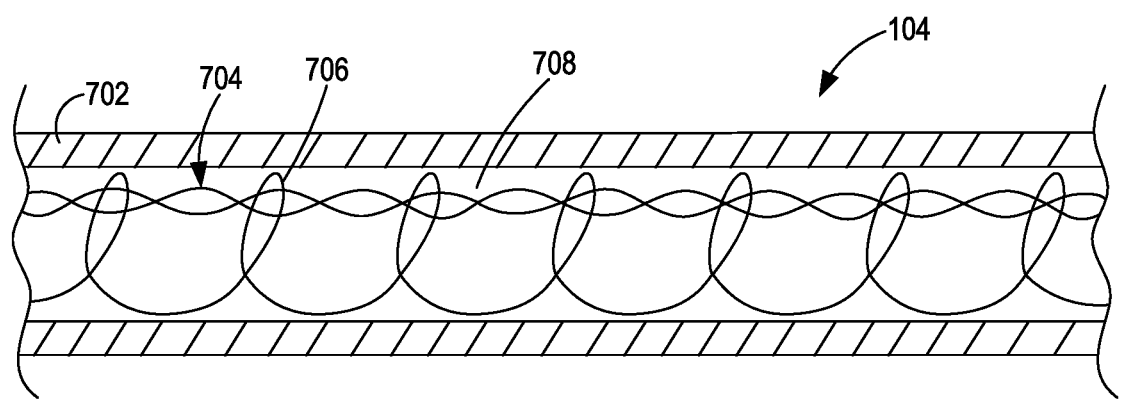
FIG. 7 is a cross-sectional view of a fourth example of an intermediate section of the implantable medical lead or lead extension where a twisted pair of conductors is present within the implantable medical lead along with a coiled conductor.

FIG. 7 also shows another example of an intermediate section of the lead 104 or lead extension where all conductors are present. In this example, the lead 104 includes a lead body 702 made of a biocompatible material such as a polyurethane. This example of the lead 104 includes a stylet lumen 708. The conductors of this example are present within the lumen 708. In this example there is one twisted pair 704 of conductors and then a set of coiled conductors 706. While a single coiled conductor 706 is shown for clarity, it will be appreciated that any number of coiled conductors, proximal connectors, and distal electrodes are possible. Therefore, in the situation where there are size coiled conductors in addition to the twisted pair 504, there can be four simultaneous channels for a combination of bipolar stimulation and sensing utilizing eight proximal connectors and eight distal electrodes. It will be appreciated that any number of conductors, proximal connectors, and distal electrodes are possible. The twisted pair 454 and the linear conductors co-exist within the lumen 508 as each of the conductors are individually insulated as previously discussed.

As with the lead 104 of FIG. 4, the configuration of the twisted pair 704 as shown in FIG. 7 may vary. For example, the twisted pair may have a number of twists per unit length that is different than that shown. Furthermore, the number of turns of coiled conductor 706 per unit length of lead 104 length may also vary from that shown.

FIG. 8 again shows another example of an intermediate section of the lead 104 or lead extension where all conductors are present. In this example, the lead 104 includes a lead body 802 made of a biocompatible material such as a polyurethane. This example of the lead 104 includes a stylet lumen 808. The conductors of this example are present within the lumen 808. In this example there is one twisted pair 804 of conductors but in this example, the twisted pair 804 is configured as a coil. As with the other conductors, it may be desirable for the twisted pair 804 to form a coil for lead extensibility and flexibility. Furthermore, it may be desirable for the twisted pair 804 to form a coil to introduce additional high frequency impedance via the added inductance of the coil for purposes of magnetic resonance imaging compatibility.

A set of coiled conductors 806 are also present in the lumen 808, and while a single coiled conductor 806 is shown for clarity, it will be appreciated that any number of coiled conductors, proximal connectors, and distal electrodes are possible. Therefore, in the situation where there are six coiled conductors in addition to the coil of the twisted pair 804, there can be four simultaneous channels for a combination of bipolar stimulation and sensing utilizing eight proximal connectors and eight distal electrodes. It will be appreciated that any number of conductors, proximal connectors, and distal electrodes are possible in this example. The twisted pair 804 and the linear conductors co-exist within the lumen 808 as each of the conductors are individually insulated as previously discussed.

Figure 8:
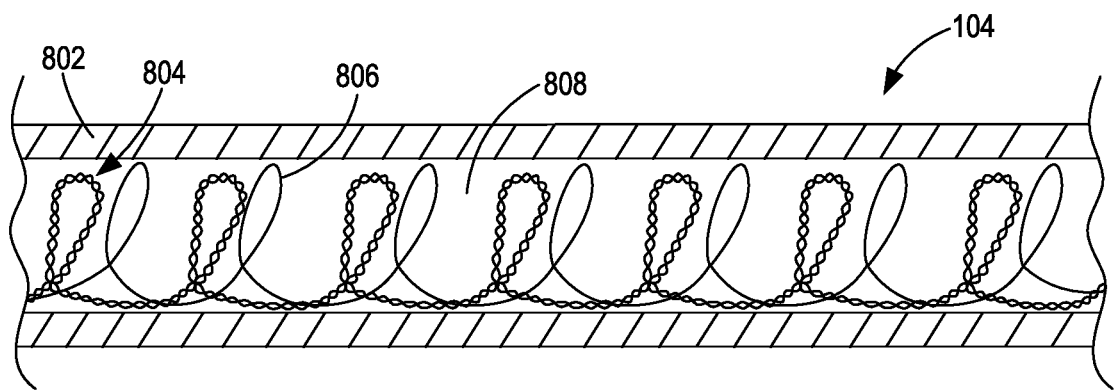
FIG. 8 is a cross-sectional view of a fifth example of an intermediate section of the implantable medical lead or lead extension where a twisted pair of conductors is present within the implantable medical lead along with a coiled conductor.

As with the lead 104 of FIG. 4, the configuration of the twisted pair 804 as shown in FIG. 8 may vary. For example, a number of twists per unit length of a turn of the coiled twisted pair 804 may differ from that shown. Furthermore, the number of turns of the coiled twisted pair 804 per unit length of lead 104 length may also vary from that shown. The number of turns of the coiled conductors 806 per unit length of lead 104 length may also vary from that shown.

Figure 9:
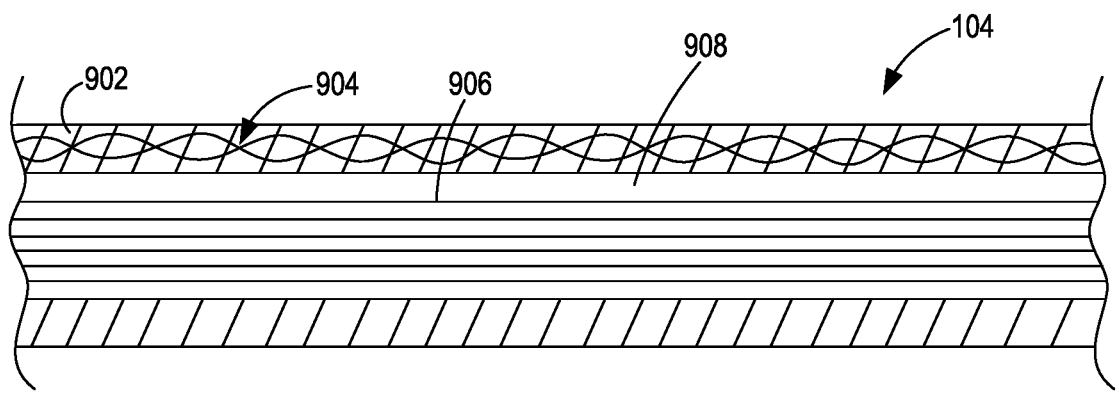
FIG. 9 is a cross-sectional view of a sixth example of an intermediate section of the implantable medical lead or lead extension where a twisted pair of conductors is present within a lead body of the implantable medical lead.

FIG. 9 shows an example of an intermediate section of the lead 104 or lead extension where all conductors are present. In this example, the lead 104 includes a lead body 902 made of a biocompatible material such as a polyurethane. This example of the lead 104 includes a stylet lumen 908. In this example there is one twisted pair 904 of conductors and then a set of six linear conductors 906. These linear conductors 906 of this example are present within the lumen 908. However, the twisted pair 904 is not present within the lumen 908 but is instead encapsulated within the lead body 902 which can be achieved via a reflow process or an injection molding process of the lead body material onto the pre-existing twisted pair 904. With the twisted pair 904 and the six conductors 906, there can again be four simultaneous channels for a combination of bipolar stimulation and sensing utilizing eight proximal connectors and eight distal electrodes. It will be appreciated that any number of conductors, proximal connectors, and distal electrodes are possible. The linear conductors co-exist within the lumen 408 as each of the conductors are individually insulated as previously discussed, and the two conductors of the twisted pair 904 are also individually insulated to avoid creating a short circuit from contact with each other.

The configuration of the twisted pair 904 as shown in FIG. 9 may vary. For example, the twisted pair may have a number of twists per unit length that is different than that shown. For instance, the ranges specific for the example of FIG. 4 may also apply for the example of FIG. 9. It will also be appreciated that additional conductors may also be encapsulated within the lead body 904. For instance, one or more of the conductors 906 may be present in the lead body 902 rather than being present in the lumen 908. Additionally, it will be appreciated that more than one twisted pair may be present within the lead body 902.

As discussed above, implantable medical leads and/or lead extensions may include at least one twisted pair of conductors to provide for EMI noise attenuation. While this is particularly applicable to circumstances where low level signals are being sensed in an environment where larger level signals or other noise may also be in proximity, there is also applicability to stimulation channels.

While embodiments have been particularly shown and described, it will be understood by those skilled in the art that various other changes in the form and details may be made therein without departing from the spirit and scope of the invention.

What is claimed is:

1. An implantable medical lead, comprising:
 a lead body;
 a first proximal connector located on a proximal end of the lead body;
 a second proximal connector located on the proximal end of the lead body and spaced apart from the first proximal connector;
 a first distal electrode located on a distal end of the lead body;
 a second distal electrode located on the distal end of the lead body and spaced apart from the first distal electrode; and
 a twisted pair of first and second conductors with insulation separating the first and second conductors, the twisted pair being present within the lead body, the first conductor of the twisted pair electrically connecting the first proximal connector and the first distal electrode, and the second conductor of the twisted pair electrically connecting the second proximal connector to the second distal electrode, wherein the twisted pair ranges from one twist per inch to one twist per two inches.

2. The implantable medical lead of claim 1, further comprising:
 a third proximal connector located on the proximal end of the lead body;
 a fourth proximal connector located on the proximal end of the lead body and spaced apart from the first proximal connector;
 a third distal electrode located on the distal end of the lead body;
 a fourth distal electrode located on the distal end of the lead body and spaced apart from the first distal electrode;
 a third conductor within the lead body and electrically connecting the third proximal connector and the third distal electrode; and
 a fourth conductor within the lead body and electrically connecting the fourth proximal connector to the fourth distal electrode.

3. The implantable medical lead of claim 2, wherein the third and fourth conductors are linear within the lead body.

4. The implantable medical lead of claim 2, wherein the third and fourth conductors form a second twisted pair with insulation separating the third and fourth conductors of the twisted pair.

5. The implantable medical lead of claim 4, wherein the twisted pair of the first and second conductors has a different number of twists per a unit length than the number of twists per the unit length of the third and fourth conductors.

6. The implantable medical lead of claim 1, wherein the twisted pair is in a linear configuration.

7. The implantable medical lead of claim 1, wherein the twisted pair is configured as a coil.

8. The implantable medical lead of claim 1, wherein the lead body defines a lumen and wherein the twisted pair is located in the lumen.

9. The implantable medical lead of claim 1, wherein the twisted pair is encapsulated in the lead body.

10. An implantable medical system, comprising:
an implantable medical device including electrical circuitry;
an implantable medical lead coupled to the implantable medical device, the implantable medical lead comprising:
   a lead body;
   a first proximal connector located on a proximal end of the lead body that is present within the implantable medical device, the first proximal connector being electrically coupled to the electrical circuitry;
   a second proximal connector located on the proximal end of the lead body and spaced apart from the first proximal connector, the second proximal connector being electrically coupled to the electrical circuitry;
   a first distal electrode located on a distal end of the lead body;
   a second distal electrode located on the distal end of the lead body and spaced apart from the first distal electrode; and
   a twisted pair of first and second conductors with insulation separating the first and second conductors, the twisted pair being present within the lead body, the first conductor of the twisted pair electrically connecting the first proximal connector and the first distal electrode, and the second conductor of the twisted pair electrically connecting the second proximal connector to the second distal electrode, wherein the twisted pair ranges from one twist per inch to one twist per two inches.

11. The implantable medical system of claim 10, wherein the electrical circuitry comprises sensing circuitry and wherein the first proximal connector and the second proximal connector are electrically coupled to the sensing circuitry.

12. The implantable medical system of claim 10, further comprising:
   a third proximal connector located on the proximal end of the lead body and spaced apart from the first and second proximal connectors;
   a fourth proximal connector located on the proximal end of the lead body and spaced apart from the first, second, and third proximal connectors;
   a third distal electrode located on the distal end of the lead body spaced apart from the first and second distal electrodes;
   a fourth distal electrode located on the distal end of the lead body and spaced apart from the first, second, and third distal electrodes;
   a third conductor within the lead body and electrically connecting the third proximal connector and the third distal electrode; and
   a fourth conductor within the lead body and electrically connecting the fourth proximal connector to the fourth distal electrode.

13. The implantable medical system of 12, wherein the third and fourth conductors are linear within the lead body.

14. The implantable medical system of claim 12, wherein the third and fourth conductors form a second twisted pair with insulation separating the third and fourth conductors of the twisted pair.

15. The implantable medical system of claim 14, wherein the twisted pair of the first and second conductors has a different number of twists per a unit length than the number of twists per the unit length of the third and fourth conductors.

16. The implantable medical system of claim 12, wherein the electrical circuitry further comprises stimulation circuitry and wherein the third and fourth conductors are electrically connected to the stimulation circuitry.

* * * * *